United States Patent
Kang et al.

(10) Patent No.: US 7,109,023 B2
(45) Date of Patent: *Sep. 19, 2006

(54) IMMUNOSSAY DEVICE FOR DIAGNOSING CONGESTIVE HEART FAILURE AND PREDICTING MORTALITY IN CONGESTIVE HEART FAILURE PATIENTS

(75) Inventors: Jemo Kang, Princeton, NJ (US); Kyung-ah Kim, Princeton, NJ (US); Joo Young Choi, Plainsboro, NJ (US); George Jackowski, Kettleby (CA)

(73) Assignee: Princeton BioMeditech Corporation, Princeton, NJ (US)

( * ) Notice: Subject to any disclaimer, the term of this patent is extended or adjusted under 35 U.S.C. 154(b) by 226 days.

This patent is subject to a terminal disclaimer.

(21) Appl. No.: 10/299,583

(22) Filed: Nov. 18, 2002

(65) Prior Publication Data

US 2004/0096988 A1   May 20, 2004

(51) Int. Cl.
*C12M 1/34* (2006.01)

(52) U.S. Cl. .................. 435/287.2; 422/55; 422/56; 422/58; 435/7.92; 435/7.93; 435/7.94; 435/287.7; 435/287.9; 435/805; 435/810; 435/970; 435/973; 436/514; 436/518; 436/524; 436/525; 436/169; 436/805; 436/810; 436/815

(58) Field of Classification Search .................. 422/55, 422/56, 58; 435/7.92, 7.93, 7.94, 287.2, 435/287.7, 287.9, 805, 810, 970, 973; 436/518, 436/514, 524, 525, 169, 805, 810, 815
See application file for complete search history.

(56) References Cited

U.S. PATENT DOCUMENTS

| | | | |
|---|---|---|---|
| 5,559,041 A * | 9/1996 | Kang et al. .................. 436/518 |
| 6,461,828 B1 * | 10/2002 | Stanton et al. .............. 435/7.92 |
| 6,828,107 B1 * | 12/2004 | Asada et al. ................. 435/7.1 |
| 6,897,030 B1 * | 5/2005 | Seilhamer et al. ........... 435/7.1 |
| 2004/0096449 A1 * | 5/2004 | DeBold .................... 424/146.1 |
| 2004/0096920 A1 * | 5/2004 | Davey et al. ............... 435/7.92 |

* cited by examiner

*Primary Examiner*—Christopher L. Chin
(74) *Attorney, Agent, or Firm*—Fox Rothschild LLP

(57) ABSTRACT

An immunochemical assay device for determining the presence of NT-proBNP alone or conjunctively with Cardiac Troponin I comprising a base member, an array disposed on the base member, and at least one assay indicia zone. The array comprises (i) a reservoir pad to receive sample liquid, (ii) a wicking membrane, and (iii) at least one filter zone interposed between the wicking membrane and the reservoir pad. The filter zone being operable to permit passage of any specific immunocomplex to the wicking membrane while impeding passage of larger components.

7 Claims, 4 Drawing Sheets

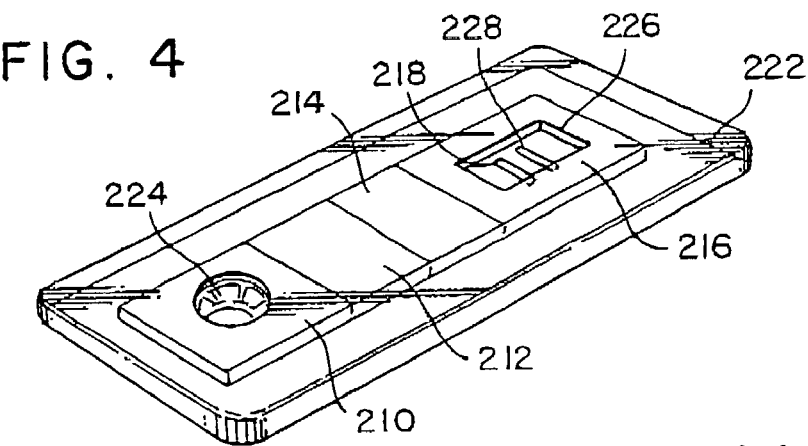
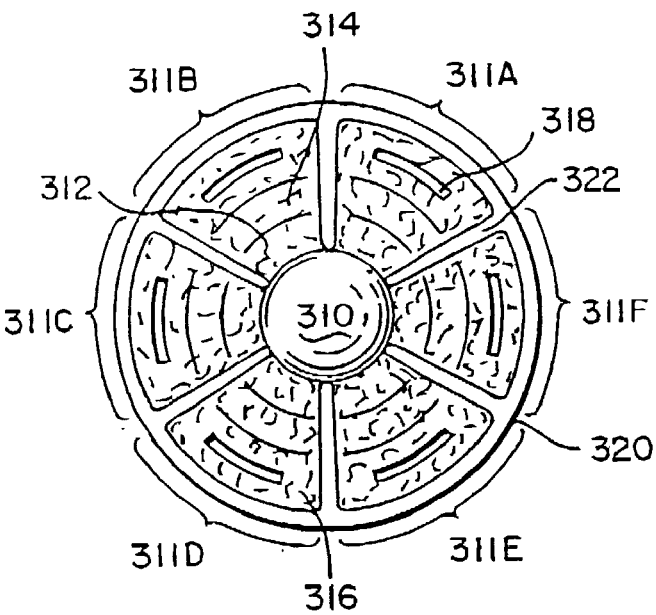
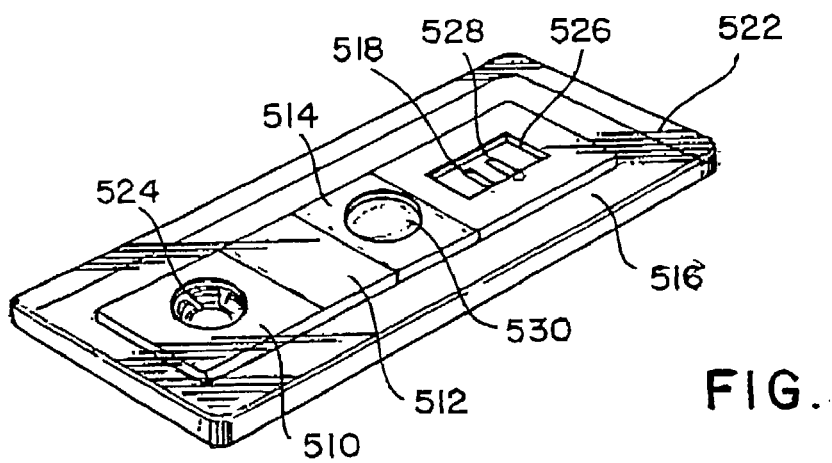

SEQUENCE LISTING

```
<160> NUMBER OF SEQ ID NOS: 1

<210> SEQ ID NO 1
<211> LENGTH: 134
<212> TYPE: PRT
<213> ORGANISM: Homo Sapiens

<400> SEQUENCE: 1

Met Asp Pro Gln Thr Ala Pro Ser Arg Ala Leu Leu Leu Leu Leu Phe
 1               5                  10                  15

Leu His Leu Ala Phe Leu Gly Gly Arg Ser His Pro Leu Gly Ser Pro
                20                  25                  30

Gly Ser Ala Ser Asp Leu Glu Thr Ser Gly Leu Gln Glu Gln Arg Asn
            35                  40                  45

His Leu Gln Gly Lys Leu Ser Glu Leu Gln Val Glu Gln Thr Ser Leu
        50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
                100                 105                 110

Phe Gly Arg Lys Met Asp Arg Ile Ser Ser Ser Ser Gly Leu Gly Cys
            115                 120                 125

Lys Val Leu Arg Arg His
        130
```

IMMUNOSSAY DEVICE FOR DIAGNOSING CONGESTIVE HEART FAILURE AND PREDICTING MORTALITY IN CONGESTIVE HEART FAILURE PATIENTS

FIELD OF THE INVENTION

The present invention comprises an improvement to a device for detection of the presence of an analyte in a sample of biological fluid through the use of immunochemical ligand-receptor reactions and specially selected, treated, and arranged filter materials, particularly to the creation of an immunoassay device for diagnosing, stratifying, and predicting mortality in patients suffering from congestive heart failure.

BACKGROUND OF THE INVENTION

Various methods for detecting the presence of an analyte in a sample of biological fluid through the use of immunochemistry have been described. In the so-called "sandwich" method, for example, a target analyte such as an antigen is "sandwiched" between a labeled antibody and an antibody immobilized onto a solid support. The assay is read by observing the presence and amount of bound antigen-labeled antibody complex. In the competition immunoassay method, antibody bound to a solid surface is contacted with a sample containing an unknown quantity of antigen analyte and with labeled antigen of the same type. The amount of labeled antigen bound on the solid surface is then determined to providen bound on the solid surface is then determialyte in the sample.

Because these and other methods discussed below can detect both antibodies and antigens, they are generally referred to as immunochemical ligand-receptor assays or simply immunoassays.

Solid phase immunoassay devices, whether sandwich or competition type, provide sensitive detection of an analyte in a biological fluid sample such as blood or urine. Solid phase immunoassay devices incorporate a solid support to which one member of a ligand-receptor pair, usually an antibody, antigen, or hapten, is bound. Common early forms of solid supports were plates, tubes, or beads of polystyrene which were well known from the fields of radioimmunoassay and enzyme immunoassay. More recently, a number of porous materials such as nylon, nitrocellulose, cellulose acetate, glass fibers, and other porous polymers have been employed as solid supports.

A number of self-contained immunoassay kits using porous materials as solid phase carriers of immunochemical components such as antigens, haptens, or antibodies have been described. These kits are usually dipstick, flow-through, or migratory in design.

In the more common forms of dipstick assays, as typified by home pregnancy and ovulation detection kits, immunochemical components such as antibodies are bound to a solid phase. The assay device is "dipped" for incubation into a sample suspected of containing unknown antigen analyte. Enzyme-labeled antibody is then added, either simultaneously or after an incubation period. The device next is washed and then inserted into a second solution containing a substrate for the enzyme. The enzyme-label, if present, interacts with the substrate, causing the formation of colored products which either deposit as a precipitate onto the solid phase or produce a visible color change in the substrate solution. Baxter et al., EP-A 0 125 118, disclose such a sandwich type dipstick immunoassay. Kali et al., EP-A 0 282 192, disclose a dipstick device for use in competition type assays.

Flow-through type immunoassay devices were designed to obviate the need for extensive incubation and cumbersome washing steps associated with dipstick assays. Valkirs et al., U.S. Pat. No. 4,632,901, disclose a device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample.

Korom et al., EP-A 0 299 359, discloses a variation in the flow-through device in which the labeled antibody is incorporated into a membrane which acts as a reagent delivery system.

The requirement of multiple addition and washing steps with dipstick and flow-through type immunoassay devices increases the likelihood that minimally trained personnel and home users will obtain erroneous assay results.

In migration type assays, a membrane is impregnated with the reagents needed to perform the assay. An analyte detection zone is provided in which labeled analyte is bound and assay indicia is read. See, for example, Tom et al., U.S. Pat. No. 4,366,241, and Zuk, EP-A 0 143 574.

The sensitivity of migration type assays is frequently reduced, however, by the presence or formation in the sample of undesirable solid components which block the passage of labeled analyte to the detection zone. Assay sensitivity also declines when migration assay devices are flooded with too much liquid sample.

Migration assay devices usually incorporate within them reagents which have been attached to colored labels, thereby permitting visible detection of the assay results without addition of further substances. See, for example, Bernstein, U.S. Pat. No. 4,770,853, May et al., WO 88/08534, and Ching et al., EP-A 0 299 428.

Among such labels are gold sol particles such as those described by Leuvering in U.S. Pat. No. 4,313,734, dye sol particles such as described by Gribnau et al., in U.S. Pat. No. 4,373,932 and May et al., WO 88/08534, dyed latex such as described by May, supra, Snyder, EP-A 0 280 559 and 0 281 327, and dyes encapsulated in liposomes by Campbell et al., U.S. Pat. No. 4,703,017. These colored labels are generally limited in terms of the immobilization methods which are suitable. Moreover, they require a relatively large amount of ligand molecule and can involve expensive reagents, thereby adding to the cost.

Luminescent assay devices such as taught by Polizzotto et al. In U.S. Pat. No. 6,184,040 utilize an image recording material exposed to liquid luminescent material to generate a readable signal. These liquid assay test devices are generally limited to generating a simple positive or negative read-out an are incapable of variable signal intensity.

Competition type assay devices such as taught by Buck in U.S. Pat. No. 6,258,548 utilize lateral flow for performing visual detection in a test sample. However, these devices are limited to a single test zone, thereby limiting the capability of the device.

DETAILED DESCRIPTION

The present invention comprises a device for detection of the presence of an analyte in a sample of biological fluid through the use of immunochemical ligand-receptor reactions and specially selected, treated, and arranged filter materials. The nature of the invention will be apparent from the following description and from the accompanying drawings in which;

FIG. 4 is a perspective view of an assay device as depicted in FIG. 2 (shown in partial phantom lines) encased in a plastic enclosure with a single aperture;

FIG. 5 is a top view of a multidirectional assay device; and

FIG. 6 is a perspective view of an assay device as depicted in FIG. 2 (shown in partial phantom lines) encased in a plastic enclosure with 2 apertures;

DETAILED DESCRIPTION OF THE INVENTION

Figure 1:
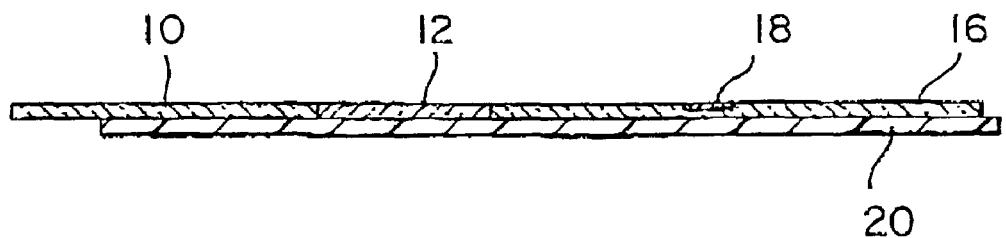
FIG. 1 is a cross sectional view of a typical unidirectional assay device.

Referring now to FIG. 1, reservoir pad 10, filter element 12, and wicking membrane 16, which contains immobilized substance defined in assay indicia zone 18, are disposed on base 20. Reservoir pad 10 has sufficient porosity and volume to receive and contain a liquid sample on which the assay is to be performed. Filter element 12 is adjacent to and contiguous across a relatively small surface of reservoir pad 10 relative to the volume of pad 10 so as to meter the passage of the liquid sample emerging from reservoir pad 10 into filter element 12.

Disposed in defined zone 18 of wicking membrane 16 is an immobilized substance which is operable to bind any specific ligand receptor complexes contained in the sample passing through filter element 12.

In this embodiment, a reagent operable to produce a specific ligand receptor complex is added to the sample where it will react to form the complex (assuming it contains the appropriate analyte) and the sample then brought into contact with reservoir pad 10. The sample migrates through filter element 12 where any unwanted components which may be present in the sample become trapped, and on into wicking membrane 16. Labeled analyte if present binds to assay indicia zone 18 producing a visibly detectable signal.

Figure 2:
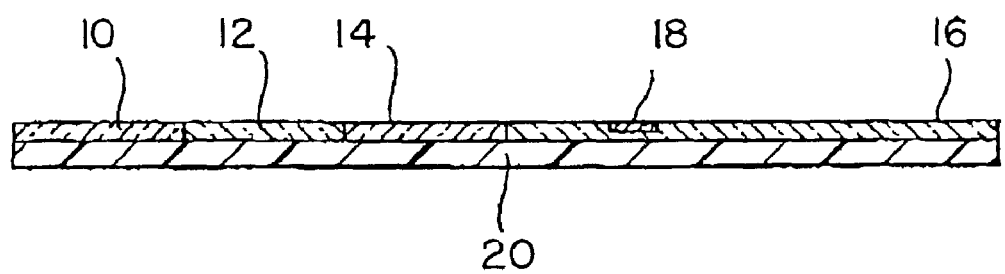
FIG. 2 is a cross sectional view of a second embodiment of a unidirectional assay device.

In the embodiment shown in FIG. 2, there is present, in addition to reservoir pad 10, filter element 12, and wicking membrane 16, second filter element 14 which is disposed on base 20. Reservoir pad 10 has sufficient porosity and volume to receive and contain a liquid sample on which the assay is to be performed. First filter element 12 is adjacent to and contiguous across a relatively small surface of reservoir pad 10 relative to the volume of pad 10 so as to meter the passage of the liquid sample emerging from reservoir pad 10 into first filter element 12. In this embodiment, a reagent operable to produce a specific ligand receptor complex is uniformly impregnated throughout first filter element 12. As liquid sample emerges from reservoir pad 10, it comes in contact with the reagent impregnated in first filter element 12 where it will react to form the specific ligand receptor complex or complexes (assuming the sample contains the appropriate analyte or analytes). The use of the first filter element as a reagent delivery system obviates the need for a separate reagent addition step.

Second filter element 14, adjacent to first filter element 12 and distal to reservoir pad 10, is operable to permit passage of any specific ligand receptor complexes contained or formed in the liquid sample but to impede passage of larger components contained therein, which components may be either present in the original sample or thereafter formed, for example in first filter element 12.

Wicking membrane 16 is adjacent to second filter element 14 and distal to first filter element 12. Wicking membrane 16 has sufficient porosity and volume to absorb a substantial proportion of the sample received in reservoir pad 10 after passage through first filter element 12 and second filter element 14.

Disposed in defined zone 18 of wicking membrane 16 is an immobilized substance which is operable to bind any specific ligand receptor complexes formed and contained in the sample passing through first filter element 12 and second filter element 14.

In use, a liquid sample is applied to reservoir pad 10 of the device shown in FIG. 2. The sample migrates through first filter element 12, wherein target analytes, if present in the sample, bind to labeled reagent. The sample continues its migration through second filter element 14 wherein any unwanted components which may be present in the sample become trapped, and on into wicking membrane 16. Labeled analyte if present then binds to assay indicia zone 18 producing a visibly detectable signal.

Alternatively, immunstatus assays can be performed by applying a sample to second filter element 14 of the device shown in FIG. 2. A buffer solution is then applied to reservoir pad 10, the solution migrates through first filter element 12 reconstituting labeled reagents therein. The solution and reagents migrate through second filter element 14 wherein target analyte if present bind to the labeled reagents, and on into wicking membrane 16. Labeled analyte if present then binds to assay indicia zone 18 producing a visibly detectable signal.

Figure 3:
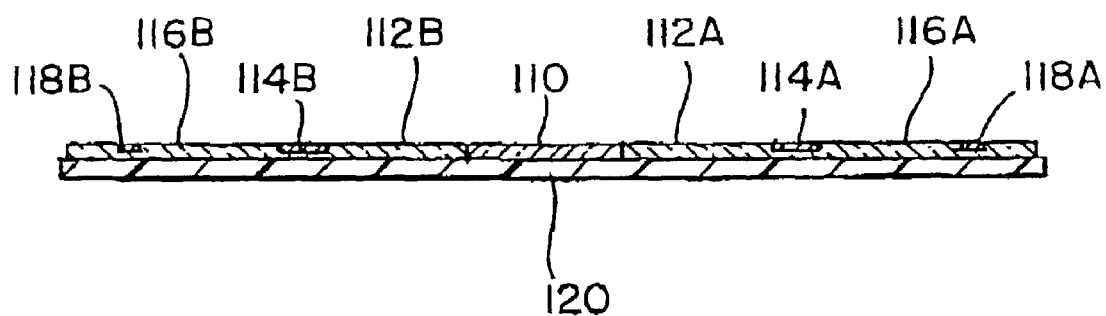
FIG. 3 is a cross sectional view of a typical bidirectional device.

Referring to FIG. 3, common reservoir pad 110, first filter elements 112A and 112B, second filter elements 114A and 114B, and wicking membranes 116A and 116B, which contain immobilized substance disposed in defined assay indicia zones 118A and 118B, are disposed on base 120. Common reservoir pad 110 has sufficient porosity and volume to receive and contain a liquid sample on which the assay is to be performed. First filter elements 112A and 112B are adjacent to and contiguous across a relatively small surface of common reservoir pad 110 with respect to the volume of pad 110 in order to meter the passage of the liquid sample from reservoir pad 110 to first filter elements 112A and 112B. Reagent operable to produce a specific ligand receptor complex is uniformly impregnated throughout first filter elements 112A and 112B. Second filter elements 114A and 114B are adjacent to first filter elements 112A and 112B respectively and distal to common reservoir pad 110, and are operable to permit passage of any specific ligand receptor complexes formed in the liquid sample but impede passage of larger components contained therein. Wicking membranes 116A and 116B have sufficient porosity and volume to absorb a substantial proportion of the sample received in common reservoir pad 110. Immobilized substance in zones 118A and 118B is operable to bind any specific ligand receptor complexes formed.

In use, a liquid sample is applied to common reservoir pad 110, the sample migrates through first filter elements 112A and 112B, wherein target analytes, if present in the sample, bind to the labeled reagents impregnated therein, through second filter elements 114A and 114B wherein any undesirable components of the fluid sample are trapped, and on into wicking membranes 116A and 116B. Target labeled analytes if present bind to assay indicia zones 118A and 118B. Thus the embodiment of FIG. 3 permits the simultaneous and independent assay of two analytes or two parallel assays for the same analyte, in each case using a single sample.

Referring to FIG. 4, an assay device such as that shown in FIG. 2 is enclosed in casing 222. Casing 222 has aperture 224 situated directly over reservoir pad 210 and viewing window 226 situated directly over assay indicia zone 218 and assay indicia control zone 228. Window 226 can be a simple aperture or can comprise a clear material which protects zones 218 and 228 but permits visual inspection. Liquid sample is added through aperture 224 and is absorbed by reservoir pad 210. It then migrates through first filter element 212 carrying the appropriate labeled reagents through second filter element 214, in which any unwanted components of the sample are trapped, and on into wicking membrane 216 in which labeled analyte, if present, binds to assay indicia zone 218. Unbound labeled reagent binds to assay indicia control zone 228. Both indicia zones 218 and 228 can be visualized through viewing window 226.

Referring to FIG. 5, base 320 which is fabricated from a moisture resistant material such as plastic is segmented into a plurality of like regions 311A, 311B, 311C, 311D, 311E, and 311F by dividers 322. Each region comprising a first filter element 312, a second filter element 314, and wicking membrane 316 all disposed in base 320 between dividers 322. The same or different reagent can be deposited in each first filter element 312, permitting either parallel tests for the same analyte or a plurality of different assays on the same sample. Each wicking membrane 316 contains an immobilized substance, as appropriate for the reagent in the first filter element associated with its corresponding wicking membrane, deposited in defined assay indicia zone 318. Common reservoir pad 310 in which the sample is deposited is centrally located with respect to the plurality of regions.

In use, a fluid sample placed on reservoir pad 310 migrates simultaneously through first filter elements 312 in which target analytes, if present, bind to labeled antibodies. The sample then passes through second filter element 314 and into wicking membranes 316 in which labeled target analytes, if present, bind to the corresponding immobilized substance in assay indicia zone 318, producing a visibly detectable signal.

The embodiment shown in FIG. 6 can be used in immunstatus assays. An assay device such as that shown in FIG. 2 is enclosed in casing 522. Casing 522 has first aperture 524 situated directly over reservoir pad 510, second aperture 530 situated directly over second filter element, and viewing window 526 situated directly over assay indicia zone 518 and assay indicia control zone 528. Window 526 can be a simple aperture or can comprise a clear material which protects zones 518 and 528 but permits visual inspection. In use, a sample (as for example serum) is applied directly onto second filter element 514 through second aperture 530. A buffer solution is then applied to reservoir pad 510 through first aperture 524, the solution migrates through first filter element 512 reconstituting labeled reagents therein. The solution and reagents migrate through second filter element 514 wherein target analyte if present bind to the labeled reagents, and on into wicking membrane 516. Labeled analyte, if present, then binds to assay indicia zone 518 producing a visibly detectable signal. Unbound labeled reagent binds to assay indicia control zone 528. Both indicia zones 518 and 528 can be visualized through viewing window 526.

Figure 7B:
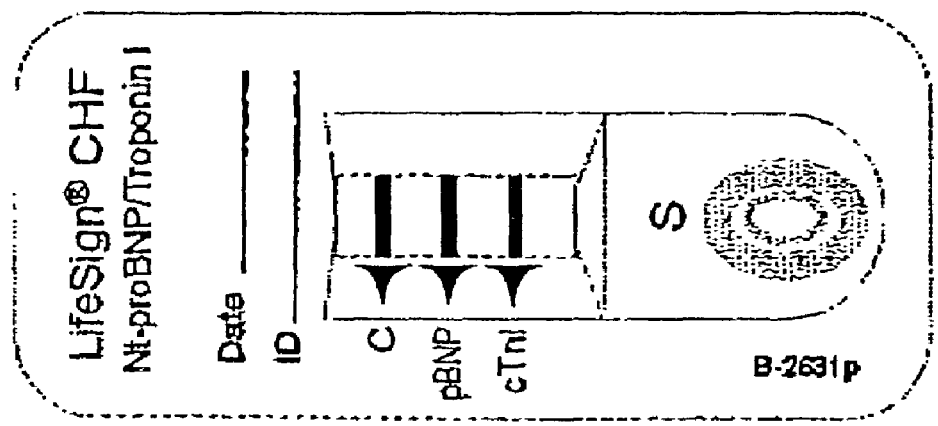
FIG. 7B is a frontal view of a device in accordance with the instant invention for determining the presence of NT-proBNP subsequent to activation.
Figure 7A:
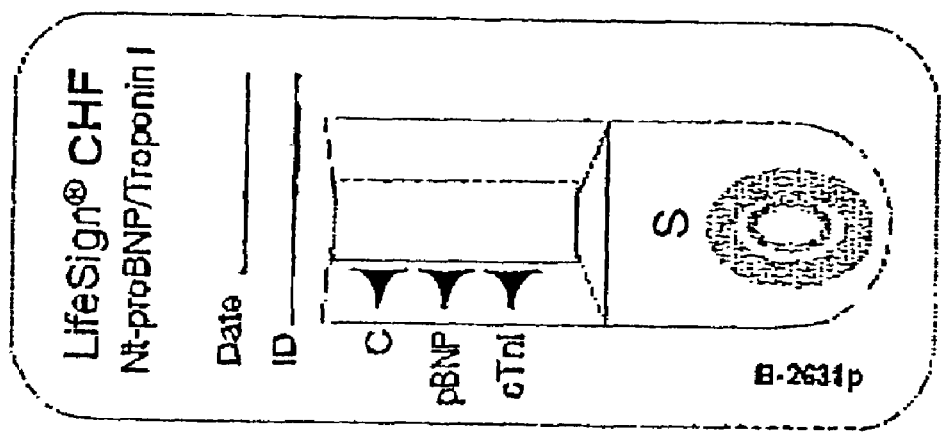
FIG. 7A is a frontal view of a device in accordance with the instant invention for determining the presence of NT-proBNP prior to activation.

Referring now to FIGS. 7A and 7B, a frontal view of a device is shown for determining the presence of NT-proBNP. Dependent upon the concentration of the protein in the sample, the line will vary in color, thereby providing a variable intensity signal for aiding in the stratification of congestive heart failure in accordance with New York Heart Association (NYHA) classification guidelines.

Figure 8B:
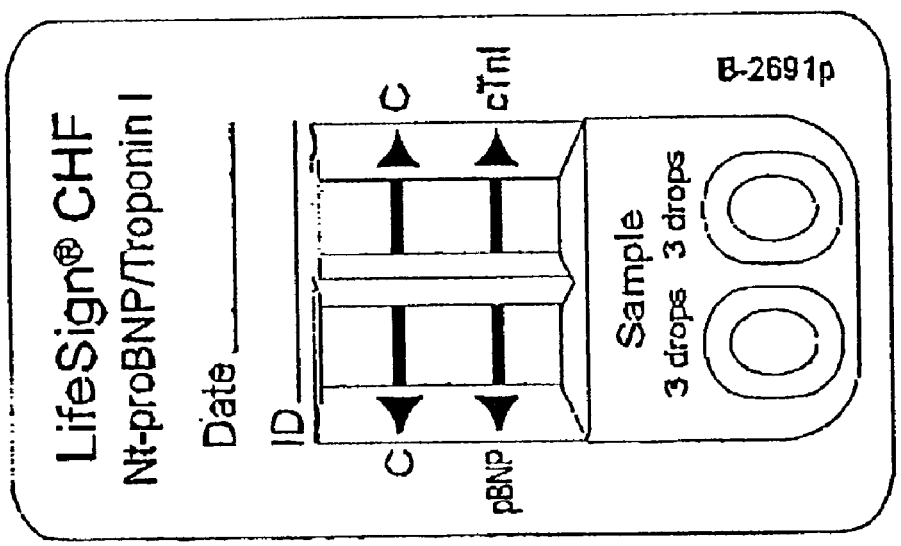
FIG. 8B is a frontal view of a device in accordance with the instant invention for determining the presence of both NT-proBNP and Cardiac Troponin I subsequent to activation.
Figure 8A:
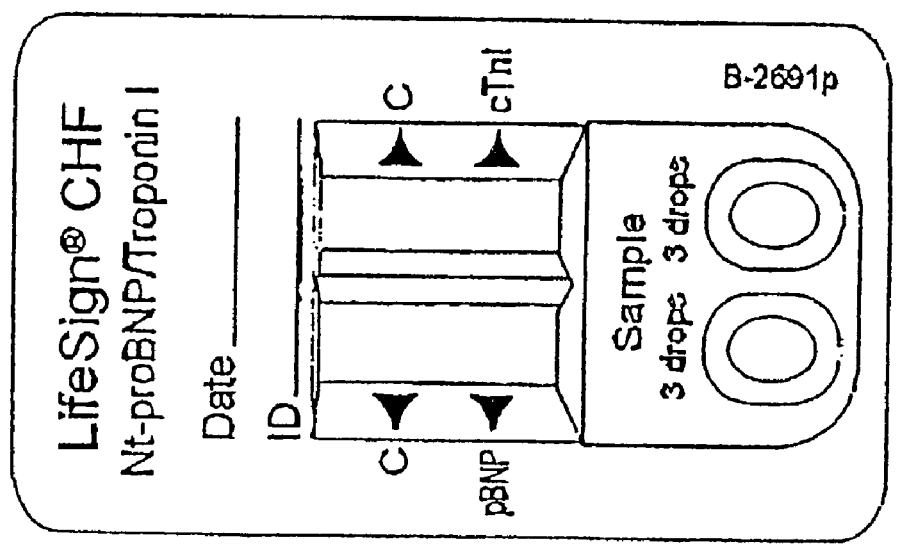
FIG. 8A is a frontal view of a device in accordance with the instant invention for determining the presence of both NT-proBNP and Cardiac Troponin I prior to activation.

Referring now to FIGS. 8A and 8B, a frontal view of a device is shown for determining the presence of both NT-proBNP and Cardiac Troponin I. Dependent upon the concentration of each of the proteins in the sample, the lines will vary in color, thereby providing a variable intensity signal for aiding in the stratification of congestive heart failure in accordance with New York Heart Association (NYHA) classification guidelines. By measuring both of these markers conjunctively, a better assessment of cardiac status can be determined, in accordance with the teachings of Stanton et al, U.S. Pat. No. 6,461,828.

Regardless of the configuration, the filter elements and pads will abut or overlap one another so as to define an interface for passage of the sample. It has been found advantageous if the wicking membrane has a high rea: thickness ratio whereas the filter element adjacent thereto has a relatively lower area:thickness ratio. To insure an adequate interface, it thus is advantageous to place the adjacent filter element in overlapping relation to the wicking membrane.

By incorporating at least one filter element before the assay indicia zone, an increase in sensitivity is achieved as compared to previous migration type assays. The filter, which preferably has been treated to reduce any inherent hydrophobicity, traps unwanted components in the fluid sample and allows unimpeded passage of labeled analyte. Thus, a proportionately greater amount of analyte binds to the assay indicia zone, and more accurate assay results are achieved.

Additionally by selecting a membrane with the appropriate texture and pore size, the second filter element can act as a controlled cell lysing system. For example in an immunstatus assay performed on a sample of whole blood it is advantageous to select as the second filter element a membrane which would maintain the integrity of whole blood cells while serum migrates through. This prevents the discoloration associated with blood cell lysis from spreading into the assay indicia zone.

When the device is used to perform an immunostatus assay, this additional filter element can also operate to receive samples directly. Generally, these assays are performed on samples of whole blood or serum which are spotted directly onto the filter. This is followed by the application of a buffer solution to the reservoir pad. Typical buffer solutions include, but are not limited to, phosphate buffer solution, saline, Tris-HCl, and water. Examples of antibodies which may be detected in this fashion include, but are not limited to, Acquired Immune Deficiency Syndrome, Rubella, Hepatitis, and Lymes.

Another source of assay sensitivity decline, sample flooding, also is avoided by the incorporation of the reservoir pad in the device. Thus the reservoir pad can hold a large quantity of sample which then is metered through the device as a result of the effective interface in the subsequent zones. This aspect of the invention makes it particularly suitable, for example, for home use where the device may be placed in a stream of urine without the need to measure the quantity of the sample applied to the device.

The reservoir pad, first filter element, second filter element, and wicking membrane are fashioned from any number of filter materials. Typical filter materials for use in the reservoir pad include, but are not limited to, low protein binding materials such as cellulose, polyesters, polyurethanes, and fiberglass with pore sizes in the range of 0.45–60 .mu.m. Typical materials for use in the first filter element include, but are not limited to, cellulosic materials (e.g., Whatman paper ET31) or fiberglass with pore sizes in the range of 0.45–60 .mu.m. Typical materials for use in the second filter element are hydrophilic materials which include, but are not limited to, polyurethane, polyacetate, cellulose, fiberglass, and nylon with pore sizes in the range of 0.45–60 .mu.m. Typical materials for use in the wicking membrane include, but are not limited to, nylon, cellulose, polysulfone, polyvinylidene difluoride, cellulose acetate, polyurethane, fiberglass, and nitrocellulose.

The entire array of pads and membranes is attached to a solid material which provides support and unity for the device. This support can be constructed from a thin sheet of glass or plastic which has been cut to a size appropriate to include entire assay contents while providing convenience to the assay user.

Another embodiment of the present invention permits the detection of multiple analytes in a single fluid sample by the presence of more than one specific type of labeled reagent and the same number of types of corresponding immobilized reagent. The device can be set up unidirectionally with multiple labeled reagents impregnated throughout one first filter element and multiple corresponding immobilized substances defined in several assay indicia zones on the wicking membrane. In the bidirectional or multidirectional embodiment, more than one set of components such as first filter element, second filter element, and wicking membrane are associated with a common reservoir.

In each case, reagents which are incorporated in the first filter element are either dried or lyophilized onto or into the element in order to allow their reconstitution upon contact with a liquid sample. Other reagents which are useful to enhance the specificity or increase the number of ligand receptor complexes created and bound and hence increase the sensitivity of the assay device, also can be included in the filter pad, or in the first of two filter pads which also will contain the reagent. These auxiliary reagents include, but are not limited to, buffers, detergents, and anticoagulants.

By including an additional assay indicia zone to serve as a control on the wicking membrane adjacent to the first zone and distal to the second filter element, the assay device presents an internal monitor which indicates whether liquid sample has migrated throughout the entire device. Assay indicia control zones generally employ immobilized antibodies (such as anti-immunoglobins) to the labeled reagents which have been added to the analyte or incorporated into the first filter element. With reference to the embodiment of FIG. 2, for example, a liquid sample migrates through the first filter element where it reconstitutes the labeled reagent and carries it to the wicking membrane. Labeled reagent which is not bound to target analyte binds to the control assay indicia zone, creating a visibly detectable indication of test completion.

The entire assay device, whether constructed as unidirectional, bidirectional, or multidirectional, can be encased in a liquid impervious plastic. This encasing normally has an aperture over the reservoir filter in order to receive sample. The entire encasement can be transparent or a portion over the analyte detection zone can be transparent in order to observe assay results. Devices encased in plastic are especially useful and convenient for use in home diagnostic kits but other materials such as treated paper also can be employed.

Additionally, the upper surface surrounding the aperture can be curved and extended downwards so as to form a cup-like receptacle which terminates at and firmly engages a portion of the reservoir pad. In this way the amount of sample introduced into the device is metered and the sample cannot bypass any components of the device.

The present invention can be used with either competition assays or sandwich assays. In competition assays, an additional inclusion of a labeled antigen (which is the same as the target antigen) is included either separately or as part of the first filter element. This labeled antigen competes with antigen from the sample for binding on the detection zone.

The diagnostic devices and methods described in the present invention can be used in any ligand-receptor reactions and are especially suited for those reactions having immunochemical components such as antibodies, antigens, and haptens. In those assays in which the detection of ligand containing molecules such as antigens or haptens is desired, both the labeled reagent and substance immobilized in the assay indicia zone are ligand binding molecules. More specifically, when the ligands are antigens, both the labeled reagents and immobilized reagents will be antibodies.

The antibodies can be either monoclonal or polyclonal, the methods of producing which are well known in the art. It is preferable to use labeled monoclonal antibodies in the first filter element and polyclonal antibodies in the assay indicia zone in order to achieve maximum binding. However, any combination of monoclonal-polyclonal antibodies can be employed. In the case of home pregnancy and ovulation predictor kits, antibodies are made to human chorionic gonadotrophin and luteinizing hormones respectively and are incorporated into the device.

In those instances in which detection of a ligand binding molecule such as an antibody is desired, labeled mouse antihuman immunoglobin G is employed as the reagent which, as noted, can be incorporated in the first filter element and antigen specific to the target antibody is immobilized in the assay indicia zone. Any natural or synthetic antigen can be employed as well as polypeptide chains which have antigenic activity. Examples of antigens which can be immobilized onto the device include, but are not limited to, Rubella, Lymes, Acquired Immune Deficiency Syndrome, Hepatitis, Toxoplasmosis, Cytomegalovirus, and Epstein Barr Virus.

In assays where the simultaneous detection of more than one antibody in a single sample is desired, since the same labelled antihuman immunoglobin (reagent) recognizes and binds to all human antibodies present in the sample, it is only necessary to incorporate antigens for each target antibody in distinct indicia zones on the wicking membrane.

The labels employed in the device can be either direct or indirect. Direct labels are preferred in that they require no additional steps in order to visualize assay results. Examples of direct labels include but are not limited to, metal sols, dye sols, particulate latex, color indicators, colored matter contained in liposomes, and nonmetal sols such as a carbon sol.

In a further aspect, the invention relates to one immunochemical label which is particularly well-suited for use in the foregoing device but which can be used in other immunological assays as well, in particular, an immunochemical label in which to an immunological ligand or ligand binding molecules is linked directly or indirectly to the surface of finely particulate carbon black.

The immunological label can be diagrammatically depicted as C.about.L or C.about.X:L in which C is the finely particulate carbon black, ".about." represents an adsorption linkage, L is a component containing a ligand- or ligand binding unit, X is a linking agent, and ":" represents a covalent bond.

L can consist of only the ligand- or ligand binding unit, in which case it is adsorbed directly onto the carbon. Alternatively, the ligand- or ligand binding unit can be bound to a bridging member either covalently or immunologically (herein designated by "*"). For example, the ligand- or ligand binding unit can be covalently bound to a linking agent such as glutaraldehyde which in turn is covalently bound to a proteinaceous bridging member such as bovine serum albumin (BSA) which in turn is adsorbed on the carbon. Likewise, avidin or streptoavidin can be linked through biotin to the ligand- or ligand binding molecule and the avidin or streptoavidin adsorbed on the carbon particles. Alternatively a primary antibody, serving as the ligand- or ligand binding unit is immunologically bound to a secondary antibody and the secondary antibody is adsorbed to the carbon particles. Typical structures of the C.about.L embodiment thus include:

C.about.{ligand},
C.about.{ligand binding molecule},
C.about.{protein:X:ligand},
C.about.{protein:X:ligand binding molecule},
C.about.{2.degree.Ab*1.degree.Ab}, and
C.about.{protein:X:2.degree.Ab*1.degree.Ab}.

In a second embodiment, a linking agent Y is both adsorbed on the carbon particle and covalently bound to the ligand- or ligand binding unit to form a label of the general formula C.about.Y:L. The linking agent Y can be a single molecular species, Y', as more fully discussed below, or can be a composite such as linking agent:protein:linking agent:

C.about.Y': {ligand},
C.about.Y': {ligand binding molecule},
C.about.Y': protein:X: {ligand}, and
C.about.Y': protein:X: {ligand binding molecule}.

It will be noted that the principal difference between the two embodiments is that in the first embodiment, a ligand, ligand binding molecule, or protein (such as an antibody, bovine serum albumin, or avidin) is adsorbed on the carbon particles whereas in the second embodiment, a member of a particular class of organic compounds serving as a linking agent is adsorbed on the carbon particles and covalently bound to a ligand, ligand binding molecule, or protein.

The foregoing carbon sols can be prepared by a number of methods. The ligand and ligand binding molecules can be simply added to a suspension of the carbon particles to produce C.about.(ligand) and C.about.(ligand binding molecule) structures. In instances in which the ligand or ligand binding molecule is bound indirectly, the full, non-carbon particle structure such as {protein:X:ligand}, {protein:X:ligand binding molecule}, {2.degree.Ab*1.degree.Ab}, or {protein:X:2.degree.Ab*1.degree.Ab} can be prepared and then added to a suspension of the carbon particles for adsorption. Alternatively, a terminal portion of the non-carbon particle structure first can be adsorbed on the carbon particles and the remainder of the non-carbon particle structure then introduced chemically. For example, a protein such as bovine serum albumin, avidin, or streptoavidin can be adsorbed on the carbon particles and then linked, using for example glutaraldehyde for bovine serum albumin or biotin for avidin or streptoavidin, to the ligand or ligand binding molecule. Similarly, a 2.degree.antibody can be adsorbed on the carbon particles and a 1.degree.antibody then joined immunologically.

Linking reagent Y' suitable for covalently-linking ligand and ligand binding molecules such as haptens, antigens, or antibodies, or for covalently-linking protein bridging groups, include imides, azides, isothiocyanates, imidoesters, and dialdehydes, as for example, maleimide, succinimide, phenylazide, glutaraldehyde, N-hydroxysuccinimide ester, phenylisothiocyanate, 4,4'-diisothiocyanostilbene-2,2'-disulfonic acid, 4-N,N-dimethylaminoazobenzene-4'-isothiocyanate, flourescein isothiocyanate, rhodamineisothiocyanate, and the like.

As in the case of the first embodiment, the complete non-carbon particle structure, prepared by reacting the ligand (or ligand binding molecule), any bridging protein, and linking agent, can be adsorbed on the surface of the finely particulate carbon black. Alternatively, the linking reagent alone first can be adsorbed on the finely particulate carbon black and then covalently bound to the ligand, ligand binding molecule, and/or bridging protein.

In any of the above procedures, it generally is desirable to add a suspending adjuvant to the aqueous suspension of the finely particulate carbon black, as for example a polyalkylene glycol or polysaccharide. As will be seen below, similar substances subsequently are added as a protective agent after linking the immunological ligand or ligand binding molecules to the finely particulate carbon black. The amount added at this stage thus is relatively small, generally being that sufficient merely to assist in the suspension of the carbon particles.

The linking reagent then is allowed to both (i) react covalently with the immunological ligand or ligand binding molecules and (ii) be adsorbed on finely particulate carbon black, either simultaneously or sequentially. While dependent on the particular linking reagent, the linking reaction generally is conducted over several hours at pH values of from about 7.0 to about 9.5.

A variety of commercially available finely particulate carbon black materials can be used such as Monarch 1,000, 120, or 880, Vulcan XC72 or XC72R, or Regal 250R or 500R. The suitability of any particular source can be readily determined by homogenating the material in buffer and measuring the optical density.

Preferably, the finely particulate carbon black with the ligand or ligand binding molecule bound covalently or passively is treated with a polyalkylene glycol or polysaccharide protective agent to minimize hydrophobicity and maximize dispersability. Suitable materials for such coating are polyethylene glycols having a molecular weight of from about 100 to about 20,000, preferably from about 5,000 to about 12,000, and protective polysaccharides such as dextran having a molecular weight of from about 10,000 to about 500,000, preferably from about 10,000 to about 50,000. This coating can be readily achieved by contacting the linked carbon black with a 0.5% to 5% weight/volume aqueous solution of the polyethylene glycol or dextran.

In a further embodiment, the immunochemical label is treated with at least one biologically acceptable ionic or nonionic surfactant, such as long chain alkyl trimethylammonium salt, sodium deoxycholate, Tritons, Tweens, etc., in a concentration range of from about 0.01 to about 0.5%. After each such treatment, of which there can be several, with the same or different types of detergent, the immunochemical label is washed to remove excess detergent.

The resulting immunochemical label then can be suspended in an aqueous media. Such aqueous suspensions of the immunochemical label are particularly useful for the fabrication of immunoassay devices, both those of the present invention and those of other structures. Preferably the aqueous suspension includes at least one buffer in order to provide a $PK_a$ at which the labeled immunological ligand or ligand binding molecule is stable; e.g., within the range of from about 6 to about 9 and preferably from about 6.5 to about 8.5.

The following examples will serve to further typify the nature of this invention but should not be construed as a limitation on the scope thereof, which is defined solely by the appended claims.

Sensitivity Procedure

Sensitivities are determined in the following examples by preparing standard solutions of human chorionic gonadotropin in concentrations of 25 mIU/ml, 50 mIU/ml, 75 mIU/ml, and 100 mIU/ml. Samples (0.15–0.20 ml) of the standard are applied to the assay device and sensitivity determined by the ability of the device to detect a given concentration of human chorionic gonadotropin.

NT-ProBNP Test

Serum or Plasma Sample Use

A. Preparation of Label

1. Gold sol particles were prepared according to a procedure well known in the art; such as Luevering (U.S. Pat. No. 4,313,734) the contents of which are incorporated herein by reference. The pH of gold sol is adjusted to 7. Goat anti-NT-proBNP antibody (Syn-x Pharma) (final conc. 4 µg/ml) is added to 50 ml of gold sol solution and stirred vigorously for 30 min at ambient temperature. 1 ml of 15% bovine serum albumin is added, and the solution is continuously stirred for approximately 15 min at ambient temperature. Colloidal gold-monoclonal antibody conjugate is recovered by centrifugation at 10,000 rpm in GSA rotor for 1 hr, discarding the supernatant and suspending the resultant pellet in 25 ml of 2% bovine serum albumin in 10 mM sodium phosphate, pH 7.5. The suspension is then spun down at 10.000 rpm for 1 hr in GSA rotor. The supernatant once again is discarded and the pellet suspended in 6 ml of 2% bovine serum albumin in 10 mM sodium phosphate, pH 7.5

B. Preparation of Strips.

a. Immobilized Substance for Test Band and Pre-Absorption of Labeled Antibody:

1. A double sided transparent tape (305 mm×25 mm size) is attached 20 mm from the bottom of a thin plastic plate (305×55 mm). A piece or strip of nitrocellulose membrane with pore size of 5 µm is cut to 305 mm×25 mm size and attached directly on the top of the double sided tape. An assay indicia zone of immobilized test line for NT-proBNP is defined on the membrane by impregnating 30 µl of solution of 1 g/ml monoclonal NT-proBNP antibody. These monoclonals were produced from supernatants for use in an NT-proBNP ELISA in pairing with Goat Polyclonal Antibodies, and are designated 6G11 and 1C3 respectively. The monoclonal antibodies are the subject of U.S. Ser. No. 10/299,606 (Express Mail Label EV140261656US) and U.S. Ser. N0. 10/300,733 (Express Mail Label EV140261611 US) filed on even date herewith, the contents of which are herein incorporated by reference, and were deposited, in accordance with the Budapest Treaty, with the American Type Culture Collection, 10801 University Blvd., Manassas, Va. 20110-2209 on Dec. 5, 2002 under Accession Numbers PTA-4844 and PTA-4845 respectively. In accordance with 37 CFR 1.808, the depositors assure that all restrictions imposed on the availability to the public of the deposited materials will be irrevocably removed upon the granting of a patent. The depositors additionally assure that the deposited materials will be replaced if viable samples cannot be dispensed by the depository. The polyclonal antibodies are the subject matter of U.S. Ser. No. 10/299,977 (Express Mail Label EV140261639US) filed on even date herewith, the contents of which are herein incorporated by reference. For control band, 1 g/ml of donkey anti-goat antibody is defined on the membrane by impregnating above the test line. After printing, the membrane is dried at ambient temperature for approximately 12 hours. The base and wicking membrane can be stored in a desiccator until further processed.

b. Preparation of Indicator Pad and Reservoir Filter Pad:

Glass fiber sheet is pretreated with a solution of 0.3% BSA, 0.2% casein and 0.5% TWEEN 20 and then air dried at room temperature. The indicator pad is prepared by wetting with a solution of colloidal gold goat anti-NT-proBNP antibody conjugate in 10 mM sodium phosphate, pH 7.5, 0.25% casein, 0.5% trehalose, 0.15% glucose, 20 mM EDTA, 0.1% sodium azide to rectangular piece of pretreated glass fiber sheet measuring 8 mm×305 mm and dried. The pad is stored dry in a desiccator until use. The glass fiber sheet for the reservoir is pretreated with the same solution for glass fiber sheet for an indicator pad and then air dried at room temperature. Indicator pad is attached to plastic base with 1 mm overlapping with the bottom of nitrocelluolse membrane and the reservoir filter pad is attached adjacent to the indicator pad. The plastic plate then is cut into a plurality of strips 55 mm in length and 7.5 mm in width so that each contains a linear array of nitrocellulose membrane, indicator pad and reservoir filter pad. The strip is assembled into a plastic device which has a result window and a sample well.

EXAMPLE 1

C. Assay Protocol and Result

When 3 drops or 120 µl of serum or plasma is applied to reservoir filter pad, a detectable signal begins to appear in the assay indicia zone after about 3 min. The assay sensitivity is 90 pg/mL.

EXAMPLE 2

Whole Blood Use

A test strip is prepared substantially in accordance with the procedure in the serum and plasma assay but the material used for the indicator pad is a blood separation filter. The assay protocol is the same. When 3 drops or 120 µl of whole blood is applied to reservoir filter pad, a detectable signal begins to appear in the assay indicia zone in about 5 min. The assay sensitivity is 90 pg/mL.

EXAMPLE 3

Whole Blood Use

A test strip is prepared substantially in accordance with the procedure in the serum and plasma assay. However, in the strip construction one more blood separation filter pad is located between indicator pad and reservoir filter pad. By doing this, the test can have better blood holding capacity.

EXAMPLE 4

NT-ProBNP and TnI Test

Two Test Strips in One Device.

To test NT-ProBNP and TnI in one test device at the same time, a double window device is used. The device has two separate sample wells and two separate test result windows on one device. In each window has each of TnI and NT-ProBNP strips. For the test protocol, 120 µl of serum, plasma, or blood is applied into each sample well. After the line develops (about 10 min.) the results are read. NT-ProBNP test strip is prepared as described above and TnI test strip is prepared as described below.

TnI Test

A. Preparation of Label

Gold sol particles are prepared as described in NT-ProBNP test, A and its pH is adjusted to 7. The monoclonal anti-TnI antibody final conc. (6 µg/ml) is added to 50 ml of the gold solution and stirred vigorously for 30 min at ambient temperature. 1 ml of 15% bovine serum albumin is added, and the solution is continuously stirred for approximately 15 min at ambient temperature. Colloidal gold-monoclonal antibody conjugate is recovered by centrifugation at 10,000 rpm in GSA rotor for 1 hr, discarding the supernatant and suspending the resultant pellet in 25 ml of 2% bovine serum albumin in 10 mM sodium phosphate buffer. The suspension is then spun down at 10,000 rpm for 1 hr in GSA rotor. The supernatant once again is discarded and the pellet suspended in 6 ml of 2% bovine serum albumin in 10 mM sodium phosphate, ph 7.5.

B. Preparation of Biotinylated Rabbit Anti TnI Antibodies

The antibody solution is added into the 50 mM: sodium carbonate, pH 8.5 to become a final concentration of 1 mg/ml and then Biotinamidocaproate N-hydroxysuccinimide ester (Sigma) in N,N-DiMethylFormamide (50 mg/ml) is added slowly while stirring (final concentration of biotin: 35 µg/ml). The solution is stirred vigorously for 30 min at ambient temperature Free Biotinamidocaproate N-Hydroxysuccinimide ester is removed by dialyzing the resulting solution in PBS.

C. Preparation of Strips a. Immobilized Substance for Test Band and Pre-absorption of Labeled Antibody A double sided transparent tape (305 mm×25 mm size) is attached to 20 mm from the bottom of the thin plastic plate (305×55 mm). A piece or strip of nitrocellulose membrane with pore size of 5 µm is cut to 305 mm×25 mm size and attached directly on the top of the double sided tape. An assay indicia zone of immobilized test line for TnI is defined on the membrane by impregnating 30 µl of solution of 1 mg/ml streptoavidin. For control band, 1 mg/ml of goat anti-mouse IgG antibody is defined on the membrane by impregnating above the test line. After printing, the membrane is dried at ambient temperature for approximately 12 hours. The base and wicking membrane can be stored in a desiccator until further processed.

b. Preparation of Indicator Pad and Reservoir Filter Pad:

A blood separation glass fiber sheet is pretreated with a solution of 0.4% BSA, 0.1% casein, and 0.07% TWEEN 20 and then air dried at room temperature. The indicator pad is prepared by wetting with a solution of colloidal gold anti-TnI antibody conjugate in 50 mM sodium carbonate, pH 9.6, 20 mM EDTA, 1% casein, 0.5% trehalose to rectangular piece of pretreated glass fiber membrane measuring 8 mm×305 mm and dried. The pad is stored dry in a desiccator until use.

A polyester sheet as a reservoir pad is pretreated with the same solution and the same way for the indicator pad and sprayed with the biotin and rabbit anti-TnI antibody conjugated solution. The pad is then dried.

The indicator pad is attached to plastic base with 1 mm overlapping with the bottom of nitrocellulose membrane and a blood separation filter pad is located below the indicator pad and then the reservoir filter pad is attached adjacent to the blood separation filter pad. The plastic plate then is cut into a plurality of strips 55 mm in length and 7.5 mm in width so that each contains a linear array of nitrocellulose membrane, indicator pad, blood separation filter pad and reservoir filter pad.

EXAMPLE 5

C. Assay Protocol and Result

When 3 drops or 120 µl of serum, plasma or blood is applied to each sample well, a detectable signal begins to appear in the assay indicia zone after about 5 min. The assay sensitivity is 0.2 ng/mL.

Two Tests in One Strip

One Strip Has Two Test Lines Including NT proBNP and TnI.

A. Preparation of Label

The labeled gold dyes are prepared as described in the NT-ProBNP test and TnI tests.

B. Preparation of Biotinylated Rabbit Anti TnI Antibodies

The biotinylated rabbit anti TnI antibodies are prepared as described in the TnI test.

C. Preparation of Strips a. Immobilized Substance for Test Band and Pre-absorption of Labeled Antibody:

A double sided transparent tape (305 mm×25 mm size) is attached to 20 mm from the bottom of the thin plastic plate (305×55 mm). A piece or strip of nitrocellulose membrane with pore size of 5 µm is cut to 305 mm×25 mm size and attached directly on the top of the double sided tape. An assay indicia zone of immobilized test lines of NT-proBNP and TnI are defined on the membrane by impregnating 30 µl of solution of 1 mg/ml monoclonal NT-proBNP antibody and 30 µl of solution of 1 mg/ml streptoavidin respectively approximately 28 mm and 33 mm from the bottom end of the strip. For control band, 1 mg/ml of donkey anti-goat IgG antibody is defined on the membrane by impregnating above the test lines, approximately 38 mm from the bottom end of the strip. After printing, the membrane is dried at ambient temperature for approximately 12 hours. The base and wicking membrane can be stored in a desiccator until further processed.

b. Preparation of Indicator Pad and Reservoir Filter Pad:

A blood separation glass fiber sheet is pretreated as described in the TnI test. The indicator pad is prepared by wetting with a solution of colloidal gold-goat anti-NT-ProBNP antibody conjugate and colloidal gold-anti-TnI antibody conjugate in 50 mM sodium carbonate, pH 9.6, 20 mM EDTA, 1% casein, 0.5% trehalose to rectangular piece of pretreated glass fiber membrane measuring 8 mm×305 mm and dried. The pad is stored dry in a desiccator until use. The reservoir pad is pretreated as described in the TnI test. The strip is constructed as described in the TnI test.

EXAMPLE 6

C. Assay Protocol and Result

When 3 drops or 120 µl of serum, plasma or blood is applied to the reservoir filter pad, a detectable signal begins to appear in the assay indicia zone after about 5 min. The assay sensitivity is 90 pg/ml for NT-proBNP and 0.2 ng/mL for TnI.

What is claimed is:

1. An immunochemical assay device comprising a base member and at least one array disposed on said base member, said array comprising:

(i) a reservoir pad having sufficient porosity and volume to receive and contain a liquid;

(ii) a wicking membrane disposed distally to said reservoir pad, said wicking membrane having sufficient porosity and volume to absorb and to wick a substantial proportion of The sample received in said reservoir pad; and (iii) at least one first filter zone which is separate and distinct from said reservoir pad and wicking membrane, and intemosed between and contiguous with said wicking membrane and said reservoir pad, said first filter zone having impregnated therein one or more labeled immunochemical components capable of binding to or competing with one or more analytes of interest in said sample to form one or more immunocomplexes, said one or more labeled immunochemical components comprises an antibody specific for amino acids 26–51 of NT-proBNP (SEQ ID No:1);

(iv) at least one second filter zone which is separate and distinct from said reservoir pad, said wicking membrane and said first filter zone, and contiguous with said wicking membrane, and said first filter zone, said second filter zone having sufficient porosity and volume to receive and containing a liquid sample on which the assay is to be performed;

at least one additional immobilized immunochemical component disposed in at least one assay indicia zone of said wicking membrane downstream of said reservoir pad and defining assay indicia, said at least one additional immobilized immunochernical component comprises an antibody specific for amino acids 1–25 of NT-proBNP (SEQ ID NO:1).

2. The assay device of claim 1 further including:

A second immobilized immunochemical component disposed in a second assay indicia zone of said wicking membrane downstream of said reservoir pad and defining assay indicia, said second immobilized immunochemical comprises an antibody specific for Cardiac Troponin I.

3. The assay device according to claim 1, for performing a competition assay, wherein said first filter zone further comprises a labeled antigen wherein the labeled antigen is a same type as a target antigen.

4. The immunochemical assay device of claim 1 wherein said one or more labeled immunochemical components comprises finely particulate carbon black and one or more immunological ligands or ligand binding molecules covalently linked to a linking reagent, said carbon black being pretreated with dextran and said linking reagent being absorbed on the surface of said dextran-treated carbon black, and wherein the linking reagent is fluorescein isothiocyanate.

5. The assay device of claim 1 wherein said at least one filter zone further comprises a filter pad wherein the filter pad was pretreated with reagents to enhance the sensitivity.

6. The assay device of claim 5 wherein said reagents are selected from the group consisting of buffers, detergents, and anticoagulants.

7. The assay device of claim 1 wherein said one or more labeled immunochemical components further comprise qualitatively or quantitatively detectable probe molecules attached or covalently linked to said immunochemical components wherein the probe molecules are selected from the group consisting of colloidal gold sol, carbon sol, fluorochromes, and luminochromes.

* * * * *